United States Patent [19]

Bod et al.

[11] Patent Number: 4,990,524

[45] Date of Patent: Feb. 5, 1991

[54] 2-THIAZOLONES IN A METHOD OF TREATING A GASTRIC ULCER

[75] Inventors: Péter Bod, Gyömro; Kálmán Harsányi, Budapest; Ferenc Trischler, Budapest; Eva Fekecs, Budapest; Béla Hegedüs, Budapest; Elemér Ezer, Budapest; Judit Matuz, Budapest; Katalin Sághy, Budapest; László Szporny, Budapest; György Hajós, Budapest; Krisztina Székely, Budapest, all of Hungary

[73] Assignee: Richter Gedeon Vegyeszeti Gyar RT., Budapest, Hungary

[21] Appl. No.: 397,488

[22] PCT Filed: Dec. 13, 1988

[86] PCT No.: PCT/HU88/00079

§ 371 Date: Jul. 21, 1989

§ 102(e) Date: Jul. 21, 1989

[87] PCT Pub. No.: WO89/05804

PCT Pub. Date: Jun. 29, 1989

[30] Foreign Application Priority Data

Dec. 14, 1987 [HU] Hungary ............... 5633/87

[51] Int. Cl.5 ................. A61K 31/425; C07D 777/34
[52] U.S. Cl. ..................... 514/369; 598/186; 598/187
[58] Field of Search ............... 548/186, 187; 514/369

[56] References Cited

U.S. PATENT DOCUMENTS 4,762,849 8/1988 Grisar .................. 514/369

OTHER PUBLICATIONS

March, Advanced Organic Chemistry pp. 788–789 (1985).
Ganapathi, Proc. Ind. Acad Sci 22A 362(1945) Abstract.

Primary Examiner—Robert Gerstl
Attorney, Agent, or Firm—Herbert Dubno; Jonathan Myers

[57] ABSTRACT

The present invention relates to a method of treating a gastric ulcer by administering a 2-thia-zolone of the formula (I),

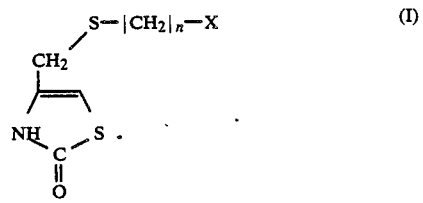

wherein
X stands for —CN, —CONH$_2$, —CO$_2$H or —CO$_2$R group, wherein R is a C$_{1-5}$alkyl group; and
n is 0, 1 or 2, with the proviso, that when X stands for CO$_2$H, CO$_2$R, n is other than 0.

4 Claims, No Drawings

2-THIAZOLONES IN A METHOD OF TREATING A GASTRIC ULCER

CROSS REFERENCE TO RELATED APPLICATIONS

This application is a national phase application of PCT/HU No. 88/00079 filed 13 Dec. 1988 and based, under the International Convention, on Hungarian national application No. 5633/87 field 14 Dec. 1987.

FIELD OF THE INVENTION

This invention relates to novel 2-thiazolone derivatives of the formula (I),

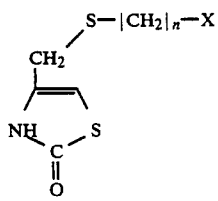

wherein
X is a —CN, —CONH$_2$, —CO$_2$H or —CO$_2$R, wherein R is a C$_{1-5}$alkyl group; and
n is 0, 1 or 2, with the proviso that, when X stands for CO$_2$H, CO$_2$R, n is other than 0,
as well as the pharmaceutical compositions containing these compounds.

When X stands for a —CO$_2$R group, then R preferably is a methyl, ethyl or propyl group.

The compounds of the formula (I) possess advantageous cytoprotective and gastric acid secretion-inhibiting effects.

BACKGROUND OF THE INVENTION

Compounds of the class of formula (I) have until now been unknown in the literature; however, the isomerizing cyclization of α-thiocyanato ketones, which may be improved by acidic or basic catalysis, is known [see e.g. J. Am. Chem. Soc. 74, 1719 (1972); or J. Chem. Soc. 1949, 2898]. According to our knowledge, this reaction type has not been used for the synthesis of α,α'-bis derivatives.

DESCRIPTION OF THE INVENTION

The invention is based on the recognition that 1,3-bis(thiocyanato)acetone of the formula (II).

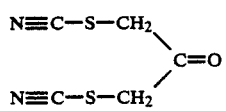

can be cyclized by using the method cited above and thereafter, the side chain of the resulting thiazole compound can further be modified in a preferable way.

According to another aspect of the invention, there is provided a process for the preparation of new compounds of the formula (I),

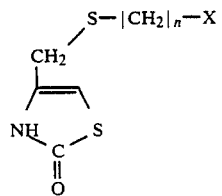

wherein
X is a —CN, —CONH$_2$, —CO$_2$H or —CO$_2$R group, wherein R is a C$_{1-5}$alkyl group; and
is 0, 1 or 2, with the proviso that, when X stands for CO$_2$H, CO$_2$R, n is other than 0,
which comprises cyclizing a compound of the formula (II), then, if desired, transforming the resulting compound of the formula (Ia),

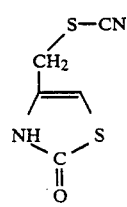

to the carbamoyl derivative of the formula (Ib),

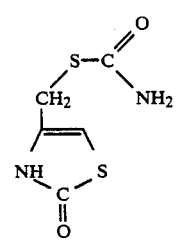

preparing therefrom by alkaline hydrolysis and S-alkylation, a compound of the formula (I), wherein n is 1 or 2 and, if desired, subjecting the side chain of the compounds thus obtained to further transformations in a known manner.

According to the process of the invention, the compound of the formula (II) is transformed to the compound of formula (Ia) or (Ib) depending on the strength of the reaction of (II) with methanol containing hydrogen chloride. The compound of the formula (Ib) is S-decarbamoylated by alkali in an aqueous alkanolic medium and then, the in situ obtained mercaptan compound is S-alkylated in a manner known per se.

The nitrile compound is further reacted by known transformations of the cyano group. In this way carboxylic acid, carboxylic acid esters, amides and other nitrogen-containing carboxylic acid derivatives (e.g. hydrazides, amidines and substituted amidines) may be prepared which in turn may be further modified.

The compound of the formula (II) used as the starting substance is known [Acta Univ. Voronegiensis 9, 167 (1937)]; it was prepared by reacting 1,3-dichloroacetone with potassium rhodanide in an aqueous-alcoholic medium.

The compound of the formula (Ia), chemically 4-thiocyanatomethyl-2(3H)-thiazolone proved to posses outstanding effects: it showed an oral ED$_{50}$ value of 0.7 mg/kg in the acidic alcohol test [A. Robert: Gastroenterology 77, 761 (1979)]; and it inhibited gastric acid secretion with even a higher oral $ED_{50}$ value of 40 mg/kg in the Shay test [Shay: Gastroenterology 5, 43 (1945)].

4-Carbamoylthiomethyl-2(3H)-thiazolone, 4-(2-cyanoethyl)thiomethyl-2(3H)-thiazolone and 4-carbamoylmethylthiomethyl-2(3H)-thiazolone also showed an advantageous effect.

Thus, the compounds according to the invention may be used as active ingredients of pharmaceutical compositions for the therapy of gastric ulcer.

SPECIFIC EXAMPLES

The invention is illustrated in detail by the following non-limiting Examples.

EXAMPLE 1

Preparation of 4-thiocyanatomethyl-2(3H)-thiazolone [compound of the formula (Ia)]

(a) 17.22 g (0.10 mol) of 1,3-bis(thiocyanato)acetone (m.p.: 94°–96° C.) are added to the stirred solution of 10 g of potassium hydrogen carbonate in 100 ml of water. The reaction mixture, which becomes mildly warm at the beginning, is stirred for 16 hours. After filtration and washing with ethanol and then with acetone and drying, 9.0 g (52.3%) of the named product are obtained, m.p.: 140°–143° C. (with decomposition). The active ingredient content of the substance is 99.1% based on the potentiometric titration with sodium hydroxide.

IR: 2180 cm$^{-1}$ [$\nu$ (C≡N)]

$^1$H-NMR (DMSO-d$_6$, $\delta$ ppm): CH$_2$: 4.1 s, Ar—H: 6.5 s, X—H: 11.5 b*.

The sulfur content of the substance is 37.5% (calculated 37.2%).

(b) After absorbing 7.3 g (0.20 mol) of gaseous hydrogen chloride in 100 ml of anhydrous methanol, 17.22 g (0.10 mol) of 1,3-bis(thiocyanato)-acetone are added and the mixture is stirred at 45° to 50° C. for 4 hours. Then, the reaction mixture is evaporated under reduced pressure until a crystalline precipitate begins to separate. After cooling down the residue, the precipitate is filtered off. After washing with methanol and drying, 8.3 g (48.3%) of the named compound are obtained with the same quality characteristics as described in Example (1a). The active ingredient content of the substance obtained is 99.0%.

EXAMPLE 2

Preparation of 4-carbamoylmercaptomethyl-2(3H)-thiazolone [compound of the formula (Ib)]

(a) After absorbing 36.5 g (1.0 mol) of gaseous hydrogen chloride in 100 ml of methanol, 17.22 g (0.10 mol) of 1,3-bis(thiocyanato)acetone are portionwise added. After ceasing of the exothermic reaction, the mixture is stirred at 40° to 42° C. for 24 hours. The evolution of methyl chloride which is violent at the beginning, slowly ceases and then completely stops. After filtration at room temperature, washing with ethanol and drying, 16.05 g (84.5%) of the named product are obtained, m.p.: 234°–246° C. (with decomposition). The active ingredient content of the substance is 98.9% based on the potentiometric titration with sodium hydroxide.

IR: 3170 cm$^{-1}$ [$\nu$ (N—H)], 1688 cm$^{-1}$ [$\nu$ (C=O) lactam], 1635 cm$^{-1}$ [$\nu$ (C=O) amide].

Analysis: calculated: C 31.55; H 3.16; N 14.74%; found: C 31.66; H 3.21; N 14.77.

(b) The process of Example (2a) is followed, except that the compound of the formula (Ia) is used as starting substance instead of the compound of the formula (II). Thus, 16.0 g (84.2%) of the named compound are obtained.

EXAMPLE 3

Preparation of 4-(2-cyanoethyl)thiomethyl-2(3H)-thiazolone 60 ml (0.60 mol) of 10N sodium hydroxide solution are added dropwise to a suspension containing 57 g (0.30 mol) of 4-carbamoylmercaptomethyl-2(3H)-thiazolone [compound of the formula (Ib)] in 150 ml of water and 90 ml of ethanol under stirring while bubbling an inert gas through the mixture. After 5 minutes, 17.5 g (0.33 mol) of acrylnitrile are added dropwise to the resulting solution at 25° to 30° C. The mixture is stirred for an additional 4 hours, then filtered to obtain a sharply clear solution which is then acidified by adding 27 ml of glacial acetic acid. The crystalline precipitate is filtered off at 15° to 20° C., washed with water and then with isopropanol and dried to give 45.8 g (76.5%) of the named compound, m.p.: 108°–111° C. The active ingredient content of the substance is 99.6%.

IR: 2260 cm$^{-1}$ [$\nu$ (C≡N)], 1660 cm$^{-1}$ [$\nu$ (C=O) lactam].

$^1$H-NMR (CDCl$_3$+DMSO-d$_6$, $\delta$ ppm: S—CH$_2$CH$_2$CN: 2.7 s, Ar—CH$_2$S: 3.5 s, Ar—H: 6.0 s, X—H: 11.2 b*.

EXAMPLE 4

Preparation of 4-carbamoylmethylthiomethyl-2(3H)-thiazolone 9.0 ml of 10N (40%) sodium hydroxide solution are added dropwise to a suspension containing 5.7 g (0.03 mol) of 4-carbamoylmercaptomethyl-2(3H)-thiazolone [compound of the formula (Ib)] in 27 ml of water and 18 ml of ethanol at 25° to 30° C. while bubbling an inert gas through the mixture. After 15 minutes, 3.0 g (0.032 mol) of chloroacetamide are added to the reaction mixture which is then stirred for 16 hours. After filtering off the insoluble material, the filtrate is acidified by adding 5 ml of glacial acetic acid. The crystalline product is filtered, washed with isopropanol and dried to obtain 4.04 g (66.0%) of the named compound, m.p.: 151°–153° C. The active ingredient content of the substance is 99.4% based on titration with alkaline metal hydroxide.

IR: 3390 cm$^{-1}$ [$\nu$ NH$_2$], 1665 cm$^{-1}$ [$\nu$ (C=O) lactam], 1630 cm$^{-1}$ [$\nu$ (C=O) amide].

$^1$H-NMR (DMSO-d$_6$, $\delta$ ppm): S—CH$_2$—CONH$_2$: 3.1 s, Ar—CH$_2$—S: 3.6 s, Ar—H: 6.2 s, NH$_2$: 7.1–7.5, b*, NH: 11.3 b*.

EXAMPLE 5

Preparation of 3-(2-oxothiazolin-4-ylmethylthio)propionic acid

A solution containing 6.01 g (0.03 mol) of 4-(2-cyanoethyl)thiomethyl-2(3H)-thiazolone in 27 g of 6N hydrochloric acid is refluxed under stirring for 4 hours. After filtration at room temperature, washing and drying, 5.16 g (78.5%) of the named compound are obtained, m.p.: 125°–127° C. The active ingredient content of the substance is 97.0% based on titration with sodium hydroxide.

IR: 3400–2000 cm$^{-1}$ [$\nu$ (X—H)], 1720 cm$^{-1}$ [$\nu$ (C=O) lactam], 1600 cm$^{-1}$ [$\nu$ (C=O) carboxyl].

$^1$H-NMR (DMSO-d$_6$, δ ppm): SCH$_2$CH$_2$COOH: 2.6 t) Ar—CH$_2$—S: 3.5 s, Ar—H: 6.2 s, X—H: 11.3 b.

EXAMPLE 6

Preparation of methyl 3-(2-oxothiazolin-4-yl-methylthio)propionate 4.39 g (0.02 mol) of 3-(2-oxothiazolin-4-yl-methylthio)propionic acid are refluxed with the mixture of 5 ml of methanol and 0.5 g of concentrated sulfuric acid for 6 hours, then the reaction mixture is poured into 10 g of ice water under stirring. The crystalline precipitate is filtered, washed and dried to give 3.97 g (85%) of the named compound, m.p.: 70°–73° C. The active ingredient content of the substance is 98.8% based on potentiometric titration with sodium hydroxide.

IR: 1725 cm$^{-1}$ [ν (C=O) ester], $^1$H-NMR (DMSO-d$_6$, δ ppm): S—CH$_2$—CH$_2$—CO: 2.6 t, Ar—CH$_2$—S: 3.5 s, O—CH$_3$: 4.0 s, Ar—H: 6.2 s, X—H: 11.2 b.

EXAMPLE 7

Pharmaceutical Composition

Preparation of tablets containing 50 mg of active ingredient each

For the preparation of 1000 tablets the following components are used:

| | |
|---|---|
| 4-thiocyanatomethyl-2(3H)-thiazolone | 50 g |
| Lactose | 210 g |
| Starch | 30 g |
| Magnesium stearate | 3 g |

The components are mixed in a mixer equipment and then compressed to tablets in a tabletting machine.

We claim:

1. A method of treating a gastric ulcer condition in an affected subject which comprises the step of administering to said subject a therapeutically effective amount of a compound of the Formula (I)

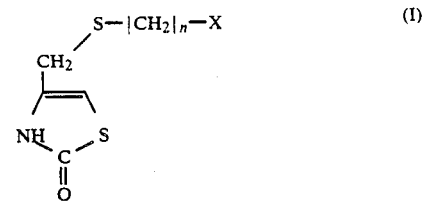

wherein
X is a —CN, —CONH$_2$, —CO$_2$H, or —CO$_2$R group;
R is a C$_1$ to C$_5$ alkyl group; and
n is 0, 1 or 2, with the proviso that when X stands for CO$_2$H or CO$_2$R, n is other than 0.

2. The method of treating a gastric ulcer condition as defined in claim 1 wherein the compound of the Formula (I) is selected from the group consisting of:
 (a) 4-thiocyanatomethyl-2(3H)-thiazolone;
 (b) 4-carbomoylthiomethyl-2(3H)-thiazolone;
 (c) 4-(2-cyanoethyl)thiomethyl-2(3H)-thiazolone; and
 (d) 4-carbamoylmethylthiomethyl-2(3H)-thiazolone.

3. The method of treating a gastric ulcer condition as defined in claim 1 wherein the compound of the Formula (I) is 4-thiocyanatomethyl-2(3H)-thiazolone.

4. The method of treating a gastric ulcer condition as defined in claim 1 wherein the compound of the Formula (I) is orally administered.

* * * * *